United States Patent [19]

DeBruin et al.

[11] 4,326,318
[45] Apr. 27, 1982

[54] ELECTRODE-ACTIVE OXYGEN MONITOR

[75] Inventors: Henderikus J. DeBruin, Bellevue Heights; Sukhvinder P. S. Badwal, Ingle Farm, both of Australia

[73] Assignee: The Flinders University of South Australia, Australia

[21] Appl. No.: 112,617

[22] Filed: Jan. 16, 1980

[30] Foreign Application Priority Data

Jan. 16, 1979 [AU] Australia ............................. PD7374

[51] Int. Cl.$^3$ ............................................. G01N 27/12
[52] U.S. Cl. ............................. 23/232 E; 204/195 S; 204/1 T; 422/98
[58] Field of Search .................... 23/232 E; 422/98; 204/195 S; 73/27 R; 338/34; 204/1 S

[56] References Cited

U.S. PATENT DOCUMENTS 4,040,929  8/1977  Bauer et al. ................... 204/195 S
4,138,881  2/1979  Isenberg ..................... 204/195 S X
4,210,509  7/1980  Obayashi et al. ............... 204/195 S Primary Examiner—Arnold Turk
Attorney, Agent, or Firm—Cushman, Darby & Cushman

[57] ABSTRACT

A method of determining the oxygen partial pressure in an atmosphere at a known temperature, in which the magnitude of a critical potential equal and opposite to the free energy of formation of an oxide of a metal such as palladium in contact with the atmosphere is determined to provide a measure of the partial pressure of oxygen. Apparatus for use in the method comprises an electrolytic cell including an electrode of the said metal, an electrolyte such as yttria stabilized zirconia having ionic oxygen mobility and means to apply a potential to the cell to modify the resistance characteristics of the electrode.

20 Claims, 7 Drawing Figures

ELECTRODE-ACTIVE OXYGEN MONITOR

BACKGROUND OF THE INVENTION

1. Field of the Invention

The present invention relates to a method for the measurement of oxygen partial pressures in an atmosphere by means of an electrode-active oxygen sensor and to devices for use in such method.

2. Prior Art

One type of electrode-active oxygen sensor has been disclosed in our copending U.S. patent application Ser. No. 42,229. This type of sensor, which will be referred to hereinafter as a "2-pole, zero ΔE sensor", consists of a metal (1)/solid electrolyte/metal (2) electrolytic cell in which, in its preferred form metal (1) is a palladium foil and metal (2) is a platinum foil.

Such a cell has a quantitative sensitivity towards the partial pressure of oxygen in an atmosphere and the use of the sensor for measuring such partial pressures relies on the detection of a thermodynamic transition temperature (hereinafter referred to as a critical temperature $T_c$), at which the free energy for the formation of palladium oxide becomes zero on a scale relative to the standard hydrogen electrode. Below $T_c$, the sensor is in the so-called high resistivity mode (referred to as "hrm") and the cell's resistance is substantially higher than is the resistance at temperatures above the critical temperature, at which temperatures the sensor is in the so-called low resistivity mode (referred to as "lrm").

In a preferred mode of operation, the temperature of the sensor is raised to put it into lrm (about 900° C.). A decreasing linear temperature ramp is then applied and the temperature is noted at which the change lrm - hrm becomes obvious. At this temperature, the resistivity increases excessively compared with the linear rate due to the fall in temperature. This temperature is the critical temperature at which the free energy of formation of the oxide of the active-metal electrode becomes zero and is uniquely related to the oxygen partial pressure of the atmosphere being measured.

The "2 - pole, zero ΔE sensor" operates at zero externally applied potential, and its operation is limited by the temperature condition of the environment. Thus it is not possible to use such a sensor to determine fractional partial pressures in ambient temperatures greater than about 855° C. Furthermore the sensitivity at low oxygen pressures ($p_{O2} < 10^{-4}$ atm) is impeded by the high resistivity of the solid electrolyte at temperatures less than 400° C.

OBJECT OF THE INVENTION

An object of the present invention is to provide an electrode-active oxygen sensor which has an extended temperature range of operation compared to previously devised electrode-active oxygen sensors.

A further object is to provide a method for determining oxygen partial pressures in an atmosphere using such sensors.

SUMMARY OF THE INVENTION

According to the broad aspect, the present invention provides a method of determining the partial pressure of oxygen in an atmosphere at a known temperature, the method comprising applying a varying potential between a first metal electrode and a second metal electrode of an electrolytic cell located in said atmosphere, said electrodes being separated by an electrolyte having ionic oxygen mobility, monitoring the resistance between said first metal electrode and a third metal electrode of said electrolytic cell insulated from said second metal electrode, measuring the magnitude of a critical potential between said first and third electrodes at which a substantial change in the said resistance occurs, such critical potential being equal and opposite to the free energy of formation of an oxide of the first electrode metal at the said known temperature, whereby a quantitative determination of the partial pressure of oxygen in said atmosphere can be made.

According to a preferred aspect, the present invention provides a method of determining the partial pressure of oxygen in an atmosphere at a known temperature, the method comprising applying a potential ramp between a first metal electrode and a second metal electrode of an electrolytic cell located in said atmosphere, said electrodes being separated by an electrolyte having ionic oxygen mobility, measuring the resistance between said first metal electrode and a third metal electrode of said electrolytic cell insulated from said second metal electrode as a function of the applied potential between said first metal electrode and the second metal electrode, observing the magnitude of a critical potential between said first and third electrodes at which a substantial change in the said resistance occurs, such critical potential being equal and opposite to the free energy of formation of an oxide of the first electrode metal at the said known temperature, whereby a quantitative determination of the partial pressure of oxygen in said atmosphere can be made.

Preferably the applied potential between said first and second electrodes relative to the said third electrode is varied at a preset linear rate. The potential equal and opposite to the free energy of formation of an oxide of said first electrode metal may be determined by measuring the potential at which there is a substantial change in impedance between said first and third electrodes.

Alternatively, the potential equal and opposite to the free energy of formation of an oxide of said first electrode metal at the ambient temperature of the said atmosphere may be determined while the potential between said first and second electrodes is being varied at a linear rate, by measuring the potential between said first and third electrodes at which there is a substantial change in the current between said first and second electrodes.

According to another method of determining the potential equal and opposite to the free energy of formation of an oxide of said first electrode at the temperature of the atmosphere being analysed, a constant current is passed between said first and second electrodes for a sufficient time to reduce said oxide to the metallic state and thereafter measuring the value of the potential between said first and third electrodes which has a zero rate of change with respect to time.

According to a further aspect, the present invention provides an apparatus for determining the partial pressure of oxygen in an atmosphere, the apparatus comprising an electrolytic cell adapted to be located in the atmosphere, said cell comprising an electrolyte having ionic oxygen mobility, a first metal electrode and a second metal electrode and arranged in use to produce a current in response to the oxygen absorbed from the atmosphere into the electrolyte, the apparatus being characterised by the provision of means to apply an electrical potential between said first and second electrodes and means to determine the potential of the cell equal and opposite to the free energy of formation of an oxide of said first electrode metal at the ambient temperature of the said atmosphere.

Preferably the cell further includes a third electrode insulated from said second metal electode, the means to determine the potential equal and opposite to the free energy of formation of said oxide of said first electrode at the ambient temperature of the said atmosphere being arranged in use to determine the potential of the cell between said first and third electrodes.

Preferably said first and second electrodes are located on opposite side walls of the electrolyte.

The means to apply the electrical potential between the first and second electrodes may comprise a potentiostat and a potential scan generator to change the potential at a linear rate.

Alternatively, the means to apply the electrical potential may comprise a current source to supply a constant current between said first and second electrodes for a sufficient time to reduce the oxide to the metallic state.

The principle on which the sensor of the present invention relies is that an applied potential acting across an electrolytic cell of the type referred to can oppose the free energy of formation of an oxide of the metal of the first, i.e. active, electrode, and thereby stop oxidation or even reduce any oxide formed, if the ambient temperature is below $T_c$ (cathodic potential), or alternatively encourage oxidation if the ambient temperature is above $T_c$ (anodic potential). The modification of the thermodynamic conditions by the external application of an electrical potential is equilavent to changing the temperature at which the free energy of formation of the oxide of the active electrode metal becomes zero.

In operation at ambient temperatures below $T_c$ (defined in the absence of an externally applied electrical potential), the temperature of the sensor of the present invention is maintained at the temperature of the atmosphere within which the sensor is located, and a linear cathodic (negative) potential-versus-time ramp is applied. The potential at which the cell converts to lrm (due to decomposition of the oxide of the metal of the active electrode) is related to the difference between the temperature of the cell and the critical temperature $T_c$, and to the partial pressure of oxygen in the atmosphere.

In operating the sensor of the present invention at ambient temperatures above $T_c$, the application of an anodic (positive) potential will convert the cell from lrm to hrm and the critical potential at which the conversion takes place is directly related to the difference between the ambient temperature of the cell and the critical temperature $T_c$ and consequently to the partial pressure of the oxygen in the atmosphere.

A cathodic potential may be applied when high oxygen partial pressures are to be measured at low temperatures and the active electrode metal is partly oxidized. An anodic potential may be applied when oxygen partial pressures are to be measured at high temperatures and the active electrode metal exists in the metallic form. Thus the nature (negative or positive) and magnitude of the applied potential can be used to match the conditions of the environment of which the oxygen partial pressure is to be measured. Thus sensors according to the present invention are applicable, under all conditions where currently known standard differential membrane cells are used.

The preferred active electrode metal is palladium. Platinum, iridium, nickel and ruthenium may also be used, but are less preferred than palladium. In principle, any metal redox couple can be used, the choice being dictated by the compatibility of the cell with the environment, the relative insulating properties of the metal oxide compared with the electrolyte, the flatness and smoothness of the active metal electrode and electrolyte contact surfaces, rate of oxidation and reduction of the active metal electrode and the polarization conditions of the metal oxide and the electrolyte. The electrolyte should be a semi-conductor with a substantial oxygen ion transference number under all conditions of temperature, oxygen concentration and the applied potential. The applied potential should never exceed the decomposition potential of the electrolyte. Such a condition will rarely arise as the applied potential in most of the temperatures and oxygen partial pressures of interest will be below the electrolyte decomposition potential.

BRIEF DESCRIPTION OF THE ACCOMPANYING DRAWINGS

Further and more detailed description of the present invention will now be made with reference to the accompanying drawings, in which.

DETAILED DESCRIPTION

Figure 1:
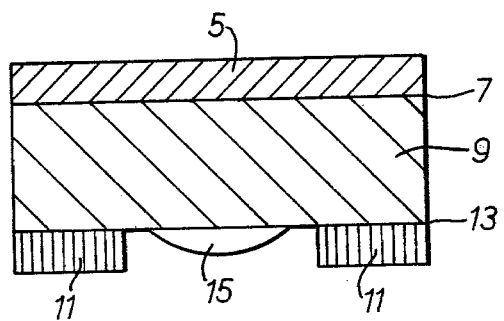
FIG. 1 is a schematic view of a basic form of an electrolytic cell used in a sensor according to the invention.

FIG. 1 shows a cell made up of an active metal electrode 5, composed of palladium in contact with a face 7 of a solid stabilized zirconia electrolyte 9. An annular platinum electrode 11 is in contact with an opposed face 13 of the electrolyte 9. A platinum spot electrode 15 is in contact with the face 13 of electrolyte 9 centrally within the annular electrode 11.

A current is passed and measured between electrodes 5 and 11, and the potential drop is measured between electrodes 5 and 15. The arrangement is such that negligible current passes through electrode 15 from electrode 11, and accordingly electrode 15 undergoes minimum polarization. Thus in effect the electrode 15 is electrically insulated from electrode 11.

The electrochemical representation of a cell of the type shown in FIG. 1 is as follows:

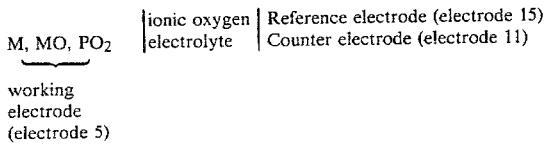

in which the active electrode metal M is shown as a bivalent metal such as palladium or nickel to simplify the explanation, and MO is the oxide formed therefrom. The electrode reaction for the active electrode metal may be written: $M + \frac{1}{2}O_2 = MO$. At *equilibrium* the free energy for the formation of the metal oxide, $\Delta G$, is related to the *thermodynamic* electrode potential, E, by:

$$\Delta G = -2EF,$$

where F is the Faraday constant ($= 9.649 \times 10^4$ C mol$^{-1}$). The thermodynamic electrode potential, E, is related to the anodic or cathodic *critical* potential, $E_c$ between electrodes 5 and 15 when the cell converts from lrm to hrm or from hrm to lrm, by correcting for geometric cell characteristics, namely $E = -(E_c - \text{cell constant})$. The free energy change for the cell under ambient conditions of temperature, T, and oxygen partial pressure $P_{O2}$, of the atmosphere to be measured is related to the standard free energy change of the M/MO couple (that is when $p_{O2} = 1$ atm), $\Delta G°$ by:

$$\Delta G = \Delta G° - RT \ln p_{O2}^{\frac{1}{2}} = -2EF$$

where R is the universal gas constant ($= 8.314$ JK$^{-1}$ mol$^{-1}$); $\Delta G°$ for active electrode metal oxides is known; E is obtained from $E_c$ when the cell converts from lrm to hrm, or vice versa, hence at the measured ambient temperature of the unknown atmosphere the oxygen partial pressure can be calculated. For example, if the active electrode metal (15) is palladium, then for $Pd + \frac{1}{2}O_2 = PdO$ $\Delta G° = -108,240 + 94.81$ T J mol$^{-1}$ and $2(E_c - \text{cell constant}) F = -108,204 + 94.81$ T $-9.573$ T $\log p_{O2}$. In practice a sensor is directly calibrated according to the relation $E_c = A + B \log p_{O2}$ (see FIG. 7). The electronic signal processor will have controls to adjust for the constants A and B, characteristic of specific sensors, such that oxygen partial pressures can be read directly from the output mode of the processor for each value of $E_c$.

If the active electrode metal (15) is nickel then for the reaction $Ni + \frac{1}{2}O_2 = NiO, \Delta G° = -244,555 + 98.53$ T J mol$^{-1}$.

The cell constant includes the potential drop between electrodes 5 and 15 due to the electrolyte resistance, plus any other side polarization phenomena. The cell constant will vary from sensor to sensor and can be calculated for each sensor assembly. From the above it will be apparent that if $E_c$ at which MO starts decomposing or M starts oxidizing is determined experimentally, $p_{O2}$ may be calculated.

There are three preferred methods of determining $E_c$, and they are as follows:

1. AC impedance measurements

Figure 2:
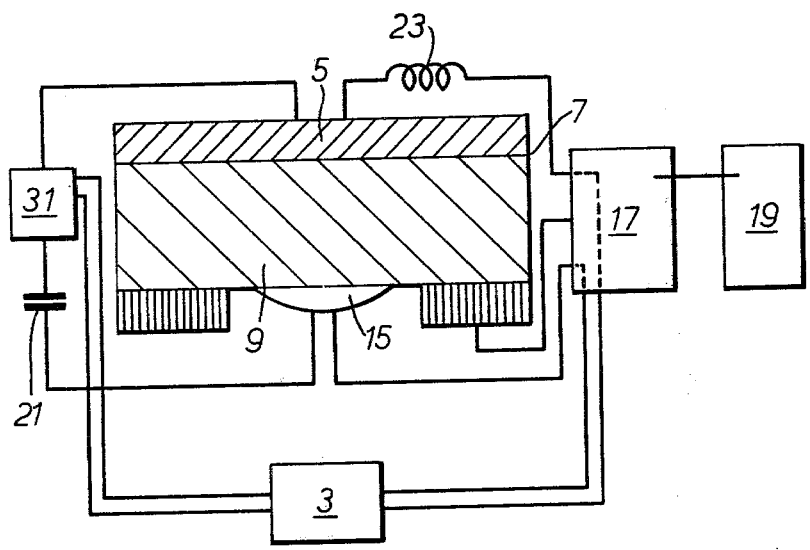
FIG. 2 is a schematic view of one embodiment of a sensor according to the invention.

In FIG. 2 a sensor is shown in which a dc potential is applied between electrodes 5 and 11 by means of a potentiostat 17. The potential is changed at a present linear rate by potential scan generator 19. The potentiostat measures the potential between electrodes 5 and 15 independently of the supply of voltage between electrodes 5 and 11. The ac impedance is measured between electrodes 5 and 15 by means of conductance bridge 31 for a constant frequency (preferably between 30 and 80 Hz). The capacitor 21 in the ac circuit is used to block any dc getting into the ac circuit and a choke 23 in the dc circuit is used to block ac signal getting into the dc circuit. These two components assist in ensuring that the measurement of the potential between electrodes 5 and 15 is insulated from interference which may arise due to the current between electrodes 5 and 11. Both potential and ac impedance between electrodes 5 and 15 are recorded on a two pen X-T, Y-T chart recorder 3. The potential (E) at which a sharp increase of resistance or an increase in the rate of change of ac impedance is observed is determined whereafter the $p_{O2}$ may be calculated. In principle, any equipment capable of applying dc potential at a linear rate and measuring ac impedance can be used.

2. Potentiostatic method

Figure 3:
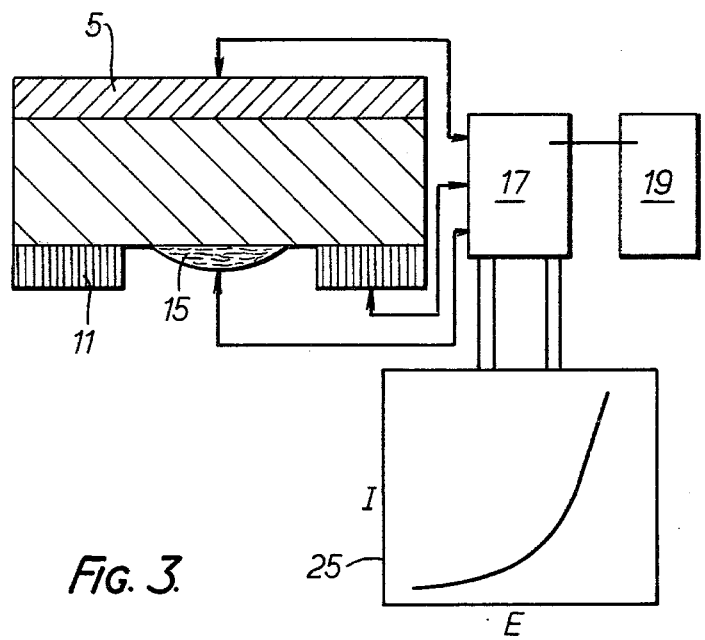
FIG. 3 is a schematic view of a second embodiment of a sensor according to the invention.

This method is similar to method 1, but instead of measuring ac impedance at constant frequency, the dc current between electrodes 5 and 11 is plotted against potential between electrodes 5 and 15 on an X-Y recorder 25 (see FIG. 3). The scan rate is varied to optimize the conditions for a given metal redox couple. At or near the decomposition potential of the metal oxide, a sharp rise in current is observed due to decomposition of the metal oxide. $E_c$ can be determined from current-potential curves and hence $p_{O2}$ may be determined.

3. Galvanostatic method

Figure 4:
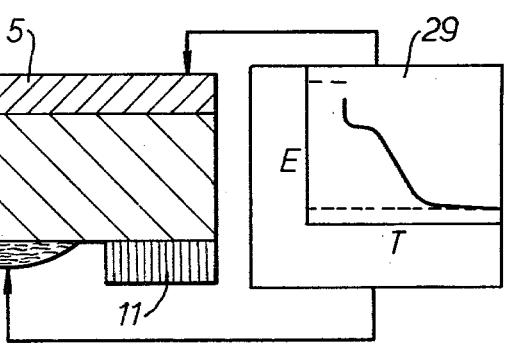
FIG. 4 is a schematic view of a third embodiment of a sensor according to the invention.

This method consists in passing a constant current from a constant current source 27 (see FIG. 4) through the electrodes 5 and 11 for sufficient time to reduce the oxide layer covering the metal phase ($MO + 2e \rightarrow M + \frac{1}{2}O_2$). After switching off the current, the potential vs. time decay curve for electrodes 5 and 15 is recorded with a storage oscilloscope 29 or X-T chart recorder. The horizontal portion of any intermediate step represents a rest potential associated with the presence of a biphasic metal-oxygen system. The potential of the rest point measured with respect to the stationary value before any current passage is E (no correction for cell constant) and is directly related to $p_{O2}$.

Figure 5:
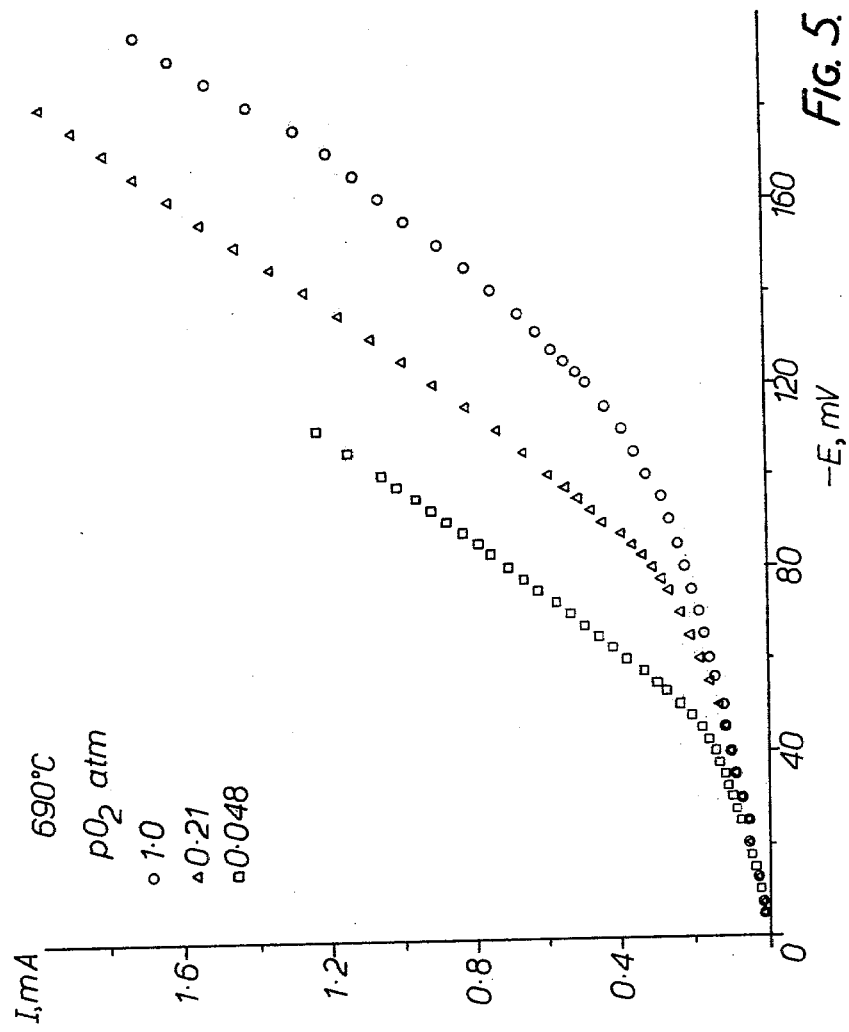
FIG. 5 is a graph illustrating current-potential curves for atmospheres tested using the cell shown in FIG. 1 embodied in the sensor shown in FIG. 3.

FIG. 5 shows the current potential curves for various gas atmospheres. The temperature of the cell used for plotting the various curves was kept constant at 690° C. and thus the cell was operated with the application of a cathodic potential. The cell includes an active metal electrode in the form of a 1000A° thick layer of palladium sputtered on to yttria stabilized zirconia (YSZ) electrolyte. The counter-electrode and the reference-electrode were made from platinum paste.

Figure 6:
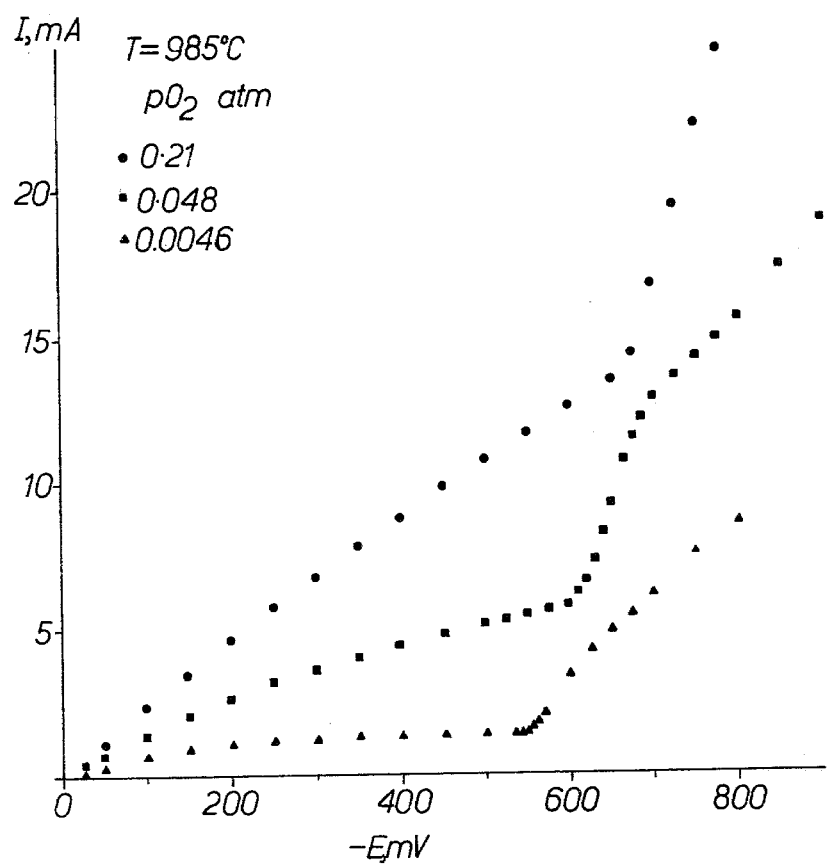
FIG. 6 is a graph illustrating current-potential curves for atmospheres tested at 985° C. with a sensor according to the invention in which nickel is the active electrode.

FIG. 6 shows the current potential curves obtained when nickel was used as the active metal electrode in contact with yttria stabilized zirconia electrolyte at 985° C. The cell with nickel electrode can be used up to 1400° C.

Figure 7:
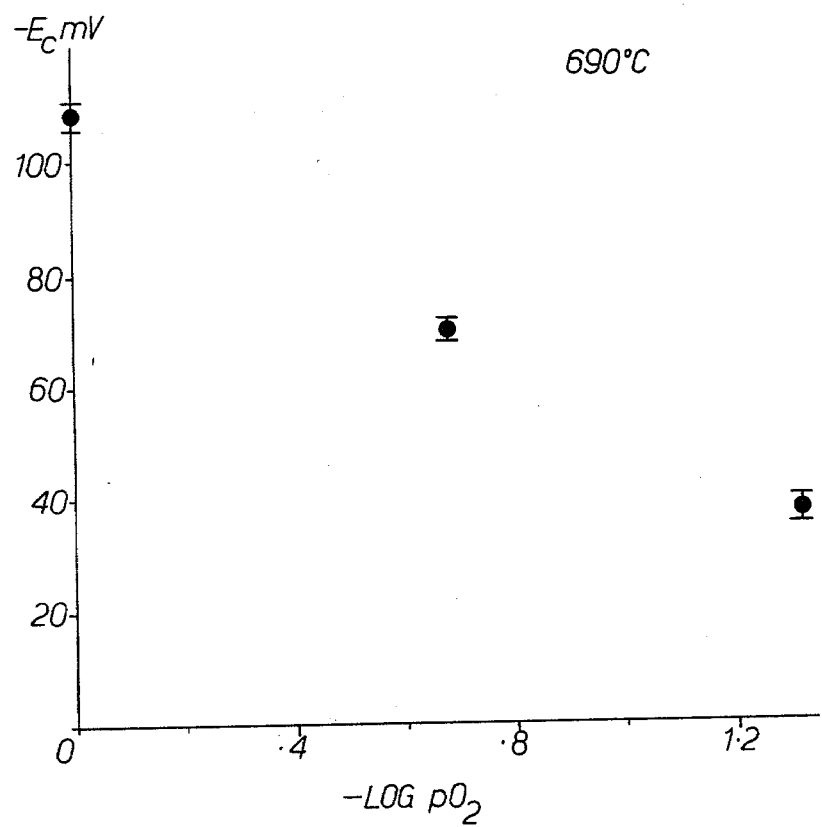
FIG. 7 is a graph of the critical potential $E_c$ at which the free energy of formation of the oxide of an active electrode becomes zero, vs log $p_{O2}$ for a palladium-/yttria stabilized zirconia cell.

FIG. 7 is a plot of $E_c$ vs. log $p_{O2}$ for Pd/YSZ cell at 690° C.

The sensor of the present invention is sensitive /to contaminants in the environment which alter the thermodynamic conditions on which the transition lrm⇌hrm is based. However, such interference will limit life expectancy of the sensor rather than its actual performance. Under such conditions, if a deterioration in response is noted, regular replacement of the sensor is recommended. This is feasible with the current invention since a relatively cheap version can be designed for given environmental conditions. In particular, a small version of the sensor can be designed for application as a combustion efficiency monitor in internal combustion engines. In such an application, the magnitude of the applied critical potential acts as a feedback signal in carburetor performance control to optimize fuel mixture injection.

The described arrangement has been advanced merely by way of explanation and many modifications may be made thereto without departing from the spirit and scope of the invention which includes every novel feature and novel combination of features herein disclosed.

We claim:

1. A method of determining the partial pressure of oxygen in an atmosphere at a known temperature, the method comprising applying a varying potential between a first metal electrode and a second metal electrode of an electrolytic cell located in said atmosphere, said electrodes being separated by an electrolyte having ionic oxygen mobility, monitoring the resistance between said first metal electrode and a third metal electrode of said electrolytic cell separated from said first metal electrode by said electrolyte and insulated from said second metal electrode, measuring the magnitude of a critical potential between said first and third electrodes at which a substantial change in the said resistance occurs, such critical potential being equal and opposite to the free energy of formation of an oxide of the first electrode metal at the said known temperature, whereby a quantitative determination of the partial pressure of oxygen in said atmosphere can be made.

2. Th method according to claim 1, wherein the applied potential between said first and second electrodes relative to the said third electrode is varied at a preset linear rate.

3. The method according to claim 1, wherein the critical potential equal and opposite to the free energy of formation of the oxide of said first electrode metal at the ambient temperature is determined by measuring the potential at which there is a substantial change in the impedance between said first and third electrodes.

4. The method according to claim 1, wherein the critical potential equal and opposite to the free energy of formation of the oxide of said first electrode metal at the ambient temperature is determined by measuring the potential between said first and third electrodes at which there is a substantial change in the current between said first and second electrodes.

5. A method according to claim 1, wherein the potential is applied in the form of a variable cathodic (negative) potential.

6. A method according to claim 1, wherein the potential is applied in the form of a variable anodic (positive) potential.

7. A method of determining the partial pressure of oxygen in an atmosphere at a known temperature, the method comprising applying a potential ramp between a first metal electrode and a second metal electrode of an electrolytic cell located in said atmosphere, said electrodes being separated by an electrolyte having ionic oxygen mobility, measuring the resistance between said first metal electrode and a third metal electrode of said electrolytic cell as a function of the applied potential between the first metal electrode and the second metal electrode, said third electrode being separated from said first electrode by said electrolyte and insulated from said second electrode, observing the magnitude of a critical potential between said first and third electrodes at which a substantial change in the said resistance occurs, such critical potential being equal and opposite to the free energy of formation of an oxide of the first electrode metal at the said known temperature, whereby a quantitative determination of the partial pressure of oxygen in said atmosphere can be made.

8. The method according to claim 7, wherein the critical potential equal and opposite to the free energy of formation of the oxide of said first electrode metal at the ambient temperature is determined by measuring the potential at which there is a substantial change in the impedance between said first and third electrodes.

9. A method according to claim 7, wherein the potential is applied in the form of a variable cathodic (negative) potential.

10. A method according to claim 7, wherein the potential is applied in the form of a variable anodic (positive) potential.

11. A method of determining the partial pressure of oxygen in an atmosphere at a known temperature, the method comprising passing a constant current between a first metal electrode and a second metal electrode of an electrolytic cell located in said atmosphere, said electrodes being separated by an electrolyte having ionic oxygen mobility, wherein said constant current is passed between said first and second electrodes for a sufficient time to reduce an oxide of the said first electrode metal to the metallic state, terminating said current, and thereafter measuring the value of a critical potential between said first metal electrode and a third metal electrode which has a zero rate of change with respect to time, said third electrode being separated from said first electrode by said electrolyte and insulated from said second electrode, such critical potential being equal and opposite to the free energy of formation of the oxide of the first electrode metal at the said known temperature, thereby providing a quantitative determination of the partial pressure of oxygen in said atmosphere.

12. An apparatus for determining the partial pressure of oxygen in an atmosphere, the apparatus comprising an electrolytic cell adapted to be located in the atmosphere, said cell comprising an electrolyte having ionic oxygen mobility, and first and second metal electrodes separated by said electrolyte, the apparatus being characterised by the provision of means to apply a variable electrical potential between said first and second electrodes and means to determine the critical potential of the cell equal and opposite to the free energy of formation of an oxide of said first electrode metal at a known temperature.

13. The apparatus according to claim 12, wherein the said first electrode metal is selected from the group consisting of palladium, platinum, iridium, nickel and ruthenium.

14. The apparatus according to claim 12, further including a third metal electrode separated from said first electrode by said electrolyte and insulated from said second metal electrode, and wherein the means to determine the critical potential of the cell equal and opposite to the free energy of formation of said oxide of said first metal electrode is arranged to determine the potential of the cell between said first and third electrodes.

15. The apparatus according to claim 14, wherein the means to apply the electrical potential comprises a potentiostat and a potential scan generator and is used to change that potential at a linear rate.

16. The apparatus according to claim 14, wherein the said first electrode metal is selected from the group consisting of palladium, platinum, tridium, nickel and ruthenium.

17. An apparatus for determining the partial pressure of oxygen in an atmosphere, the apparatus comprising an electrolytic cell adapted to be located in the atmosphere, said cell comprising an electrolyte having ionic oxygen mobility, and first and second metal electrodes separated by said electrolyte, the apparatus being characterized by the provision of means to supply a constant current between said first and second electrodes for a sufficient time to reduce an oxide of said first electrode metal to the metallic state and means to determine the critical potential of the cell equal and opposite to the free energy of formation of the oxide of said first electrode metal at a known temperature.

18. The apparatus according to claim 12, wherein the said first electrode metal is selected from the group consisting of palladium, platinum, iridium, nickel and ruthenium.

19. The apparatus according to claim 17, further including a third metal electrode separated from said first electrode by said electrolyte and insulated from said second metal electrode, and wherein the means to determine the critical potential of the cell equal and opposite to the free energy of formation of said oxide of said first electrode metal is arranged to determine the potential of the cell between said first and third electrodes.

20. The apparatus according to claim 19, wherein the said first electrode metal is selected from the group consisting of palladium, platinum, iridium, nickel and ruthenium.

* * * * *